US008899464B2

(12) United States Patent
Hueil et al.

(10) Patent No.: US 8,899,464 B2
(45) Date of Patent: Dec. 2, 2014

(54) ATTACHMENT OF SURGICAL STAPLE BUTTRESS TO CARTRIDGE

(75) Inventors: Geoffrey C. Hueil, Mason, OH (US); John V. Hunt, Cincinnati, OH (US); Venkataramanan Madakolathur Vasudevan, Cincinnati, OH (US); Israel Nur, Moshav Timmorim (IL); Greg J. Fanuele, Liberty Township, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 413 days.

(21) Appl. No.: 13/251,682

(22) Filed: Oct. 3, 2011

(65) Prior Publication Data

US 2013/0082086 A1 Apr. 4, 2013

(51) Int. Cl.
| A61B 17/068 | (2006.01) |
| A61B 17/072 | (2006.01) |
| A61B 17/064 | (2006.01) |
| A61B 17/00 | (2006.01) |

(52) U.S. Cl.
CPC . *A61B 17/07207* (2013.01); *A61B 2017/00884* (2013.01); *A61B 17/0644* (2013.01); *A61B 2017/07271* (2013.01); *A61B 17/07292* (2013.01); *A61B 2017/00477* (2013.01); *A61B 2017/07235* (2013.01); *A61B 2017/07264* (2013.01); *A61B 2017/07228* (2013.01)
USPC ....... 227/176.1; 227/19; 227/180.1; 606/139; 606/219

(58) Field of Classification Search
CPC .............. A61B 17/068; A61B 17/072; A61B 17/07207; A61B 17/07214; A61B 17/07278; A61B 17/07292

USPC .............. 227/19, 165.1, 175.2, 176.1, 178.1, 227/180.1; 606/139, 151, 153, 219
See application file for complete search history.

(56) References Cited

U.S. PATENT DOCUMENTS

| 2,303,131 A | 11/1942 | Morgan |
| 3,364,200 A | 1/1968 | Ashton et al. |

(Continued)

FOREIGN PATENT DOCUMENTS

| CA | 481943 | 2/1947 |
| EP | 328 401 | 8/1989 |

(Continued)

OTHER PUBLICATIONS

Abstract for FR2789885.

(Continued)

*Primary Examiner* — Scott A. Smith
(74) *Attorney, Agent, or Firm* — Frost Brown Todd LLC (57) ABSTRACT

A surgical instrument includes an end effector and a staple cartridge that is insertable into the end effector. The staple cartridge includes a buttress material that is selectively coupled to the staple cartridge. In some versions the buttress material may be stapled to the staple cartridge by one or more attachment staples. Such attachment staples may be inserted into staple apertures formed through an upper deck of the staple cartridge. The attachment staples may include resiliently biased legs to frictionally resist removal. In some versions the attachment staples may be sized to form an interference fit in the staple apertures. Alternatively, the attachment staples may include barbs. A staple driver may be used to decouple the attachment staples. The staple driver may include staple forming pockets to bend the legs of the attachment staple when decoupling the attachment staple.

20 Claims, 10 Drawing Sheets

(56) References Cited

U.S. PATENT DOCUMENTS

| | | |
|---|---|---|
| 3,496,940 A | 2/1970 | Steinman |
| 3,526,228 A | 9/1970 | Lyng |
| 4,222,383 A | 9/1980 | Schossow |
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,411,193 A | 5/1995 | Culp |
| 5,415,334 A | 5/1995 | Williamson, IV et al. |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Simizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,783,524 B2 | 8/2004 | Anderson et al. |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,721,930 B2 | 5/2010 | McKenna et al. |
| 7,738,971 B2 | 6/2010 | Swayze et al. |
| 7,845,533 B2 | 12/2010 | Marczyk et al. |
| 7,988,027 B2 | 8/2011 | Olson et al. |
| 8,308,041 B2* | 11/2012 | Kostrzewski ............. 227/175.1 |
| 8,308,042 B2* | 11/2012 | Aranyi ............. 227/175.1 |
| 8,371,491 B2* | 2/2013 | Huitema et al. ............. 227/176.1 |
| 8,453,652 B2* | 6/2013 | Stopek ............. 128/898 |
| 8,453,909 B2* | 6/2013 | Olson et al. ............. 227/176.1 |
| 8,529,600 B2* | 9/2013 | Woodard et al. ............. 606/219 |
| 8,584,920 B2* | 11/2013 | Hodgkinson ............. 227/176.1 |
| 8,590,762 B2* | 11/2013 | Hess et al. ............. 227/176.1 |
| 2002/0165559 A1 | 11/2002 | Grant et al. |
| 2003/0120284 A1 | 6/2003 | Palacios et al. |
| 2003/0183671 A1 | 10/2003 | Mooradian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0154403 A1 | 7/2005 | Sauer et al. |
| 2005/0245965 A1 | 11/2005 | Orban, III et al. |
| 2005/0249772 A1 | 11/2005 | Maliviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0112360 A1 | 5/2007 | De Deyne et al. |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |
| 2008/0078800 A1 | 4/2008 | Hess et al. |
| 2008/0078801 A1 | 4/2008 | Shelton, IV et al. |

(56) References Cited

U.S. PATENT DOCUMENTS

| | | | |
|---|---|---|---|
| 2008/0078802 A1 | 4/2008 | Hess et al. |
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110959 A1 | 5/2008 | Orban, III et al. |
| 2008/0114381 A1 | 5/2008 | Voegle et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0076510 A1 | 3/2009 | Bell et al. |
| 2009/0118747 A1 | 5/2009 | Bettuchi et al. |
| 2013/0068816 A1 | 3/2013 | Mandakolathur Vasudevan et al. |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| EP | 2 005 895 | 12/2008 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 96/22055 | 7/1996 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2850281.
Abstract for JP1072740.
Abstract for JP11309151.
Abstract for JP3146773.
Abstract for JP5076586.
International Search Report dated Dec. 14, 2012 for Application No. PCT/US2012/058388.
International Preliminary Report on Patentability dated Apr. 18, 2014 for Application No. PCT/US2012/058388.

* cited by examiner

ATTACHMENT OF SURGICAL STAPLE BUTTRESS TO CARTRIDGE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

Figure 1A:
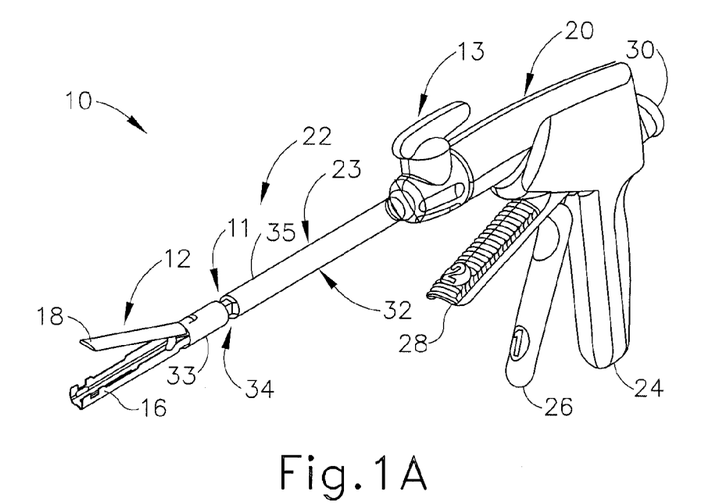
FIG. 1A depicts a perspective view of an articulating surgical instrument with an end effector in a nonarticulated position.

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical stapling and severing instrument (10) includes handle portion (20) connected to implement portion (22), the latter further comprising shaft (23) distally terminating in an articulation mechanism (11) and a distally attached end effector (12). Once articulation mechanism (11) and end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

Figure 1B:
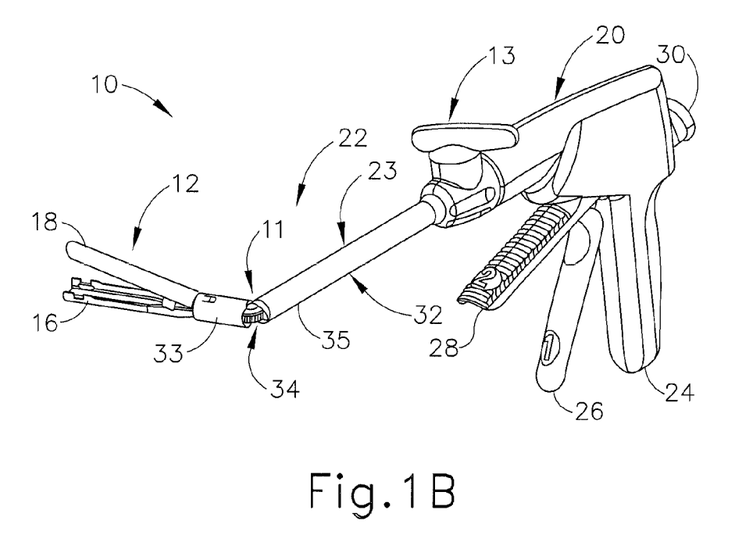
FIG. 1B depicts a perspective view of the surgical instrument of FIG. 1A with an end effector in an articulated position.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal closure ring (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
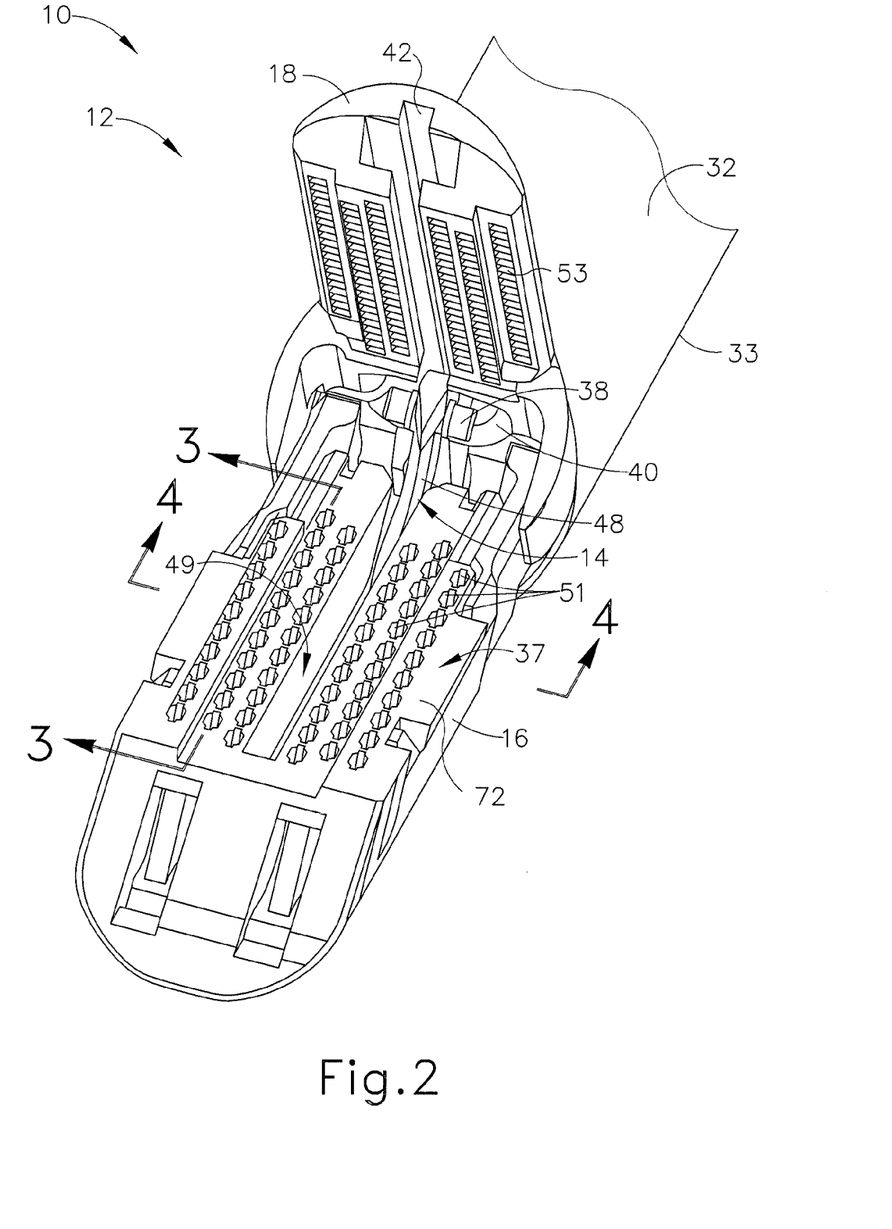
FIG. 2 depicts a perspective view of an opened end effector of the surgical instrument of FIGS. 1A-1B.
Figure 3A:
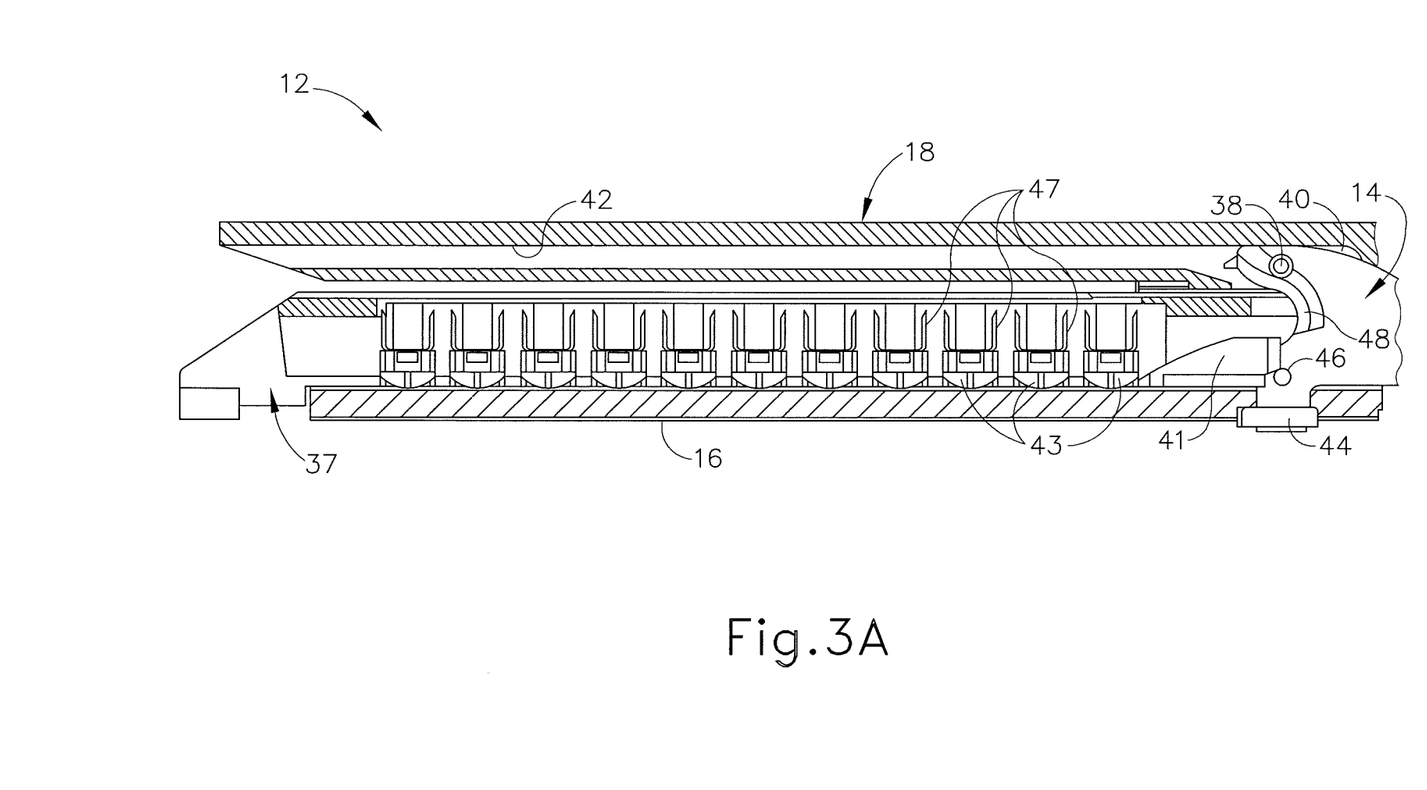
FIG. 3A depicts a side cross-sectional view of the end effector of FIG. 2, taken along line 3-3 of FIG. 2, with the firing bar in a proximal position.
Figure 3B:
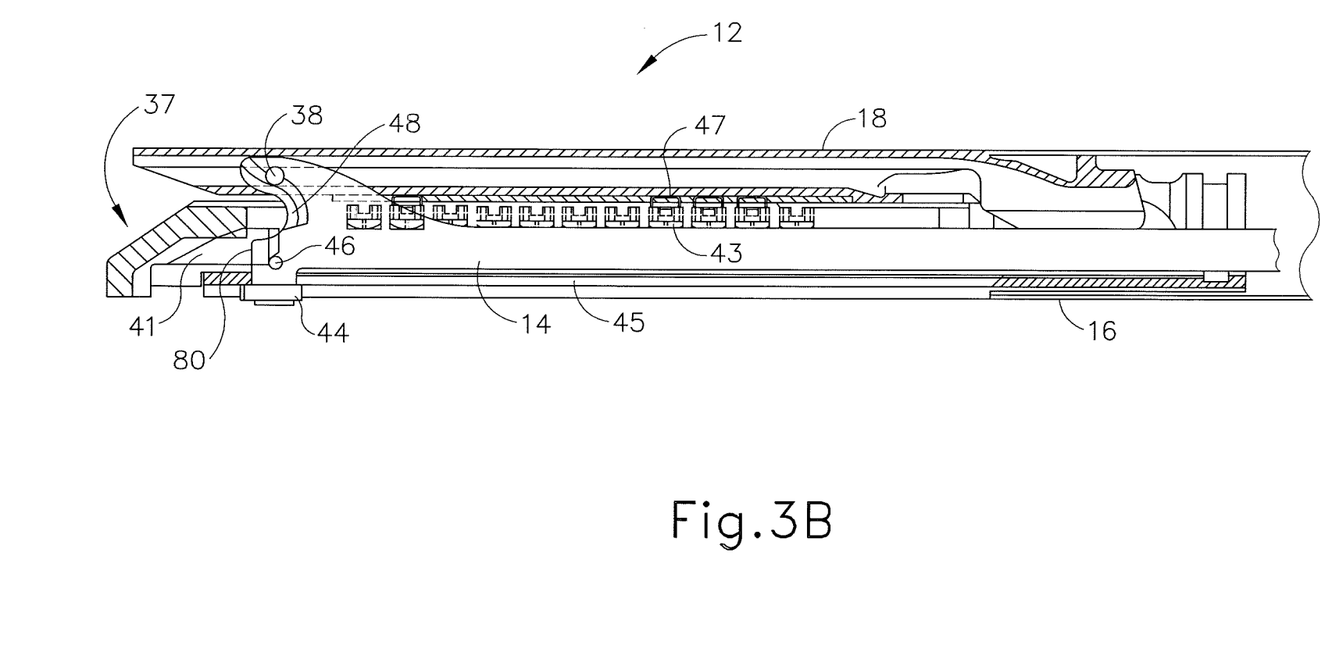
FIG. 3B depicts a side cross-sectional view of the end effector of FIG. 2, taken along line 3-3 of FIG. 2, but showing the firing bar in a distal position.
Figure 4:
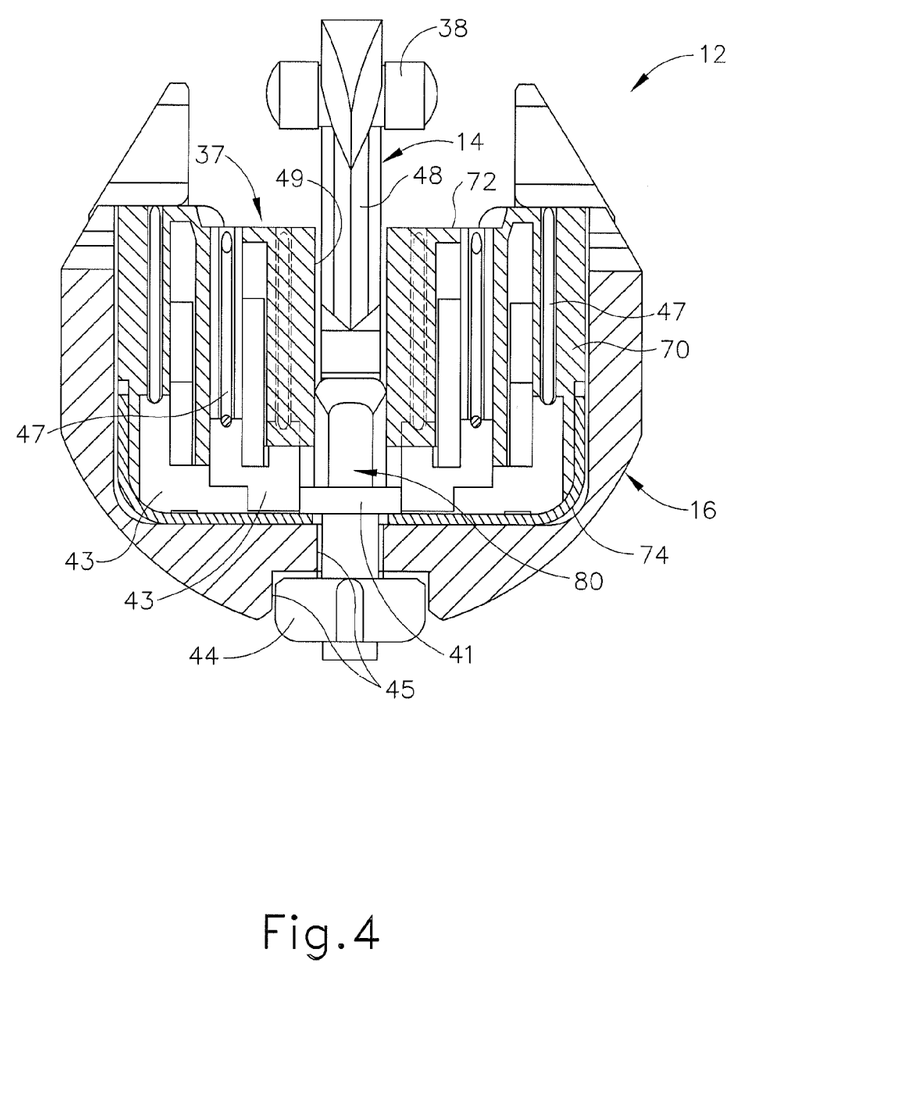
FIG. 4 depicts an end cross-sectional view of the end effector of FIG. 2, taken along line 4-4 of FIG. 2.
Figure 5:
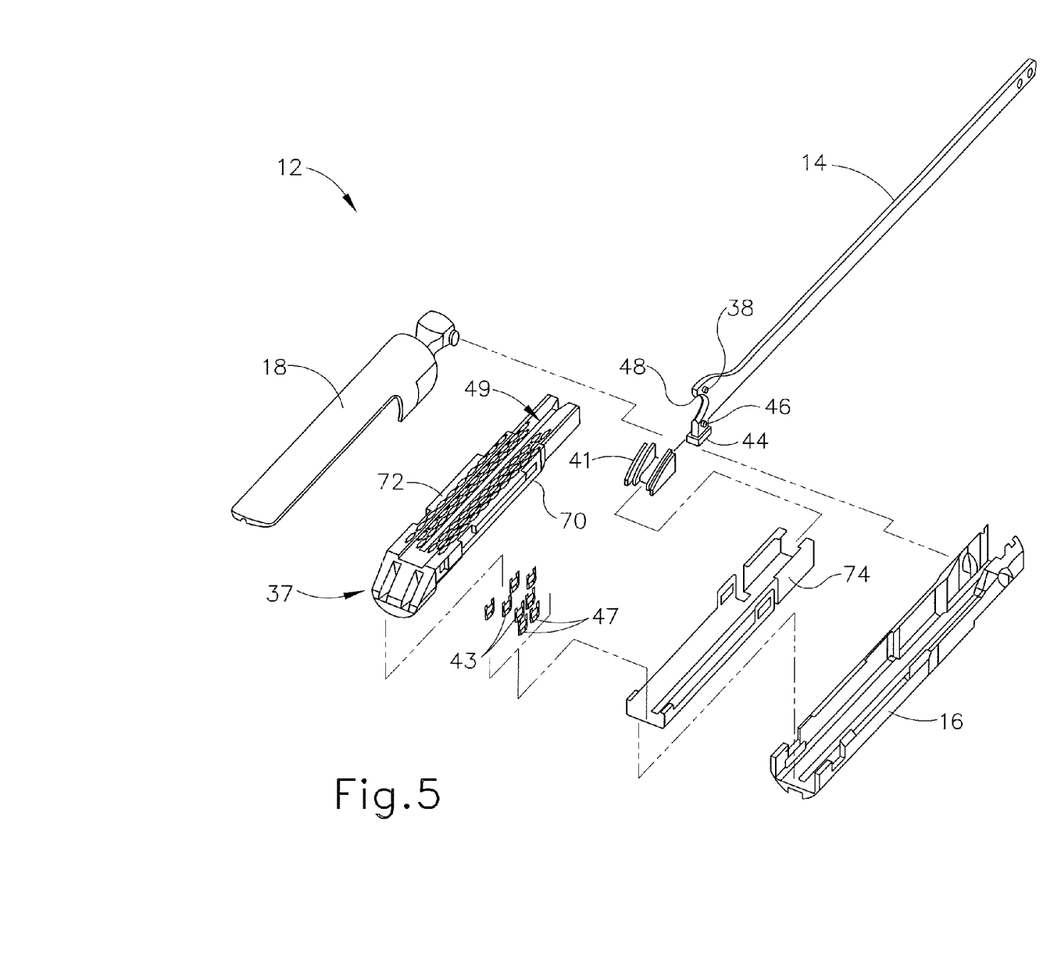
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into slot (49) within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
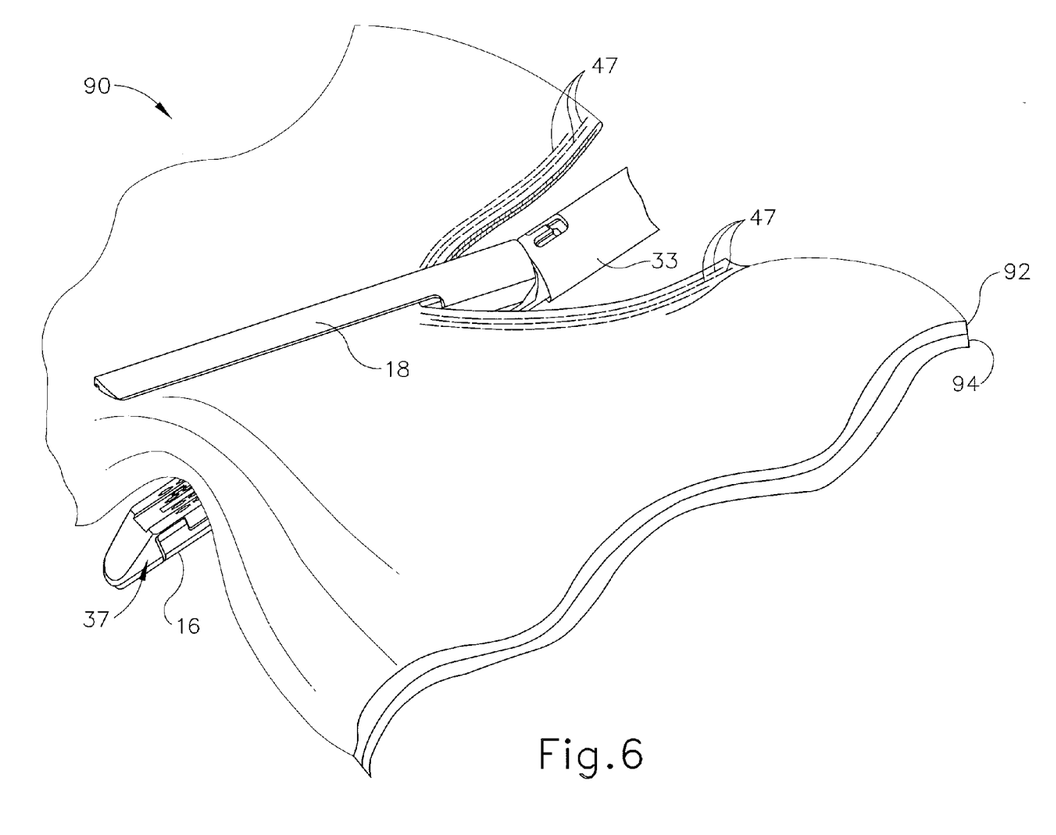
FIG. 6 depicts a perspective view of the end effector of FIG. 2, positioned at tissue and having been actuated once in the tissue.

FIG. 6 shows end effector (12) having been actuated through a single stroke through tissue (90). Cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47)

being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930.

As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Material Coupled to Staple Cartridge

Figure 7:
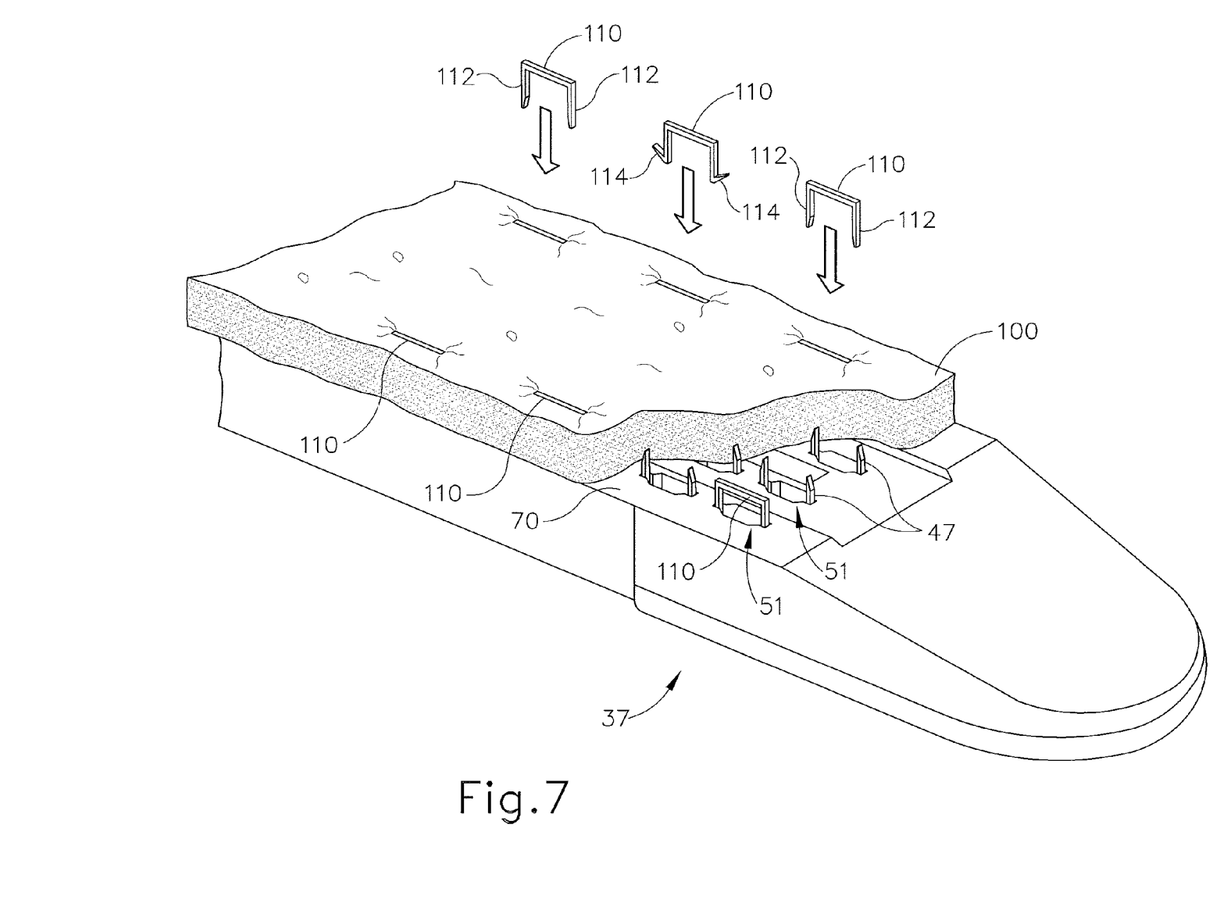
FIG. 7 depicts a perspective view of a staple cartridge for the end effector of FIG. 2 having a buttress material coupled thereto.
Figure 8A:
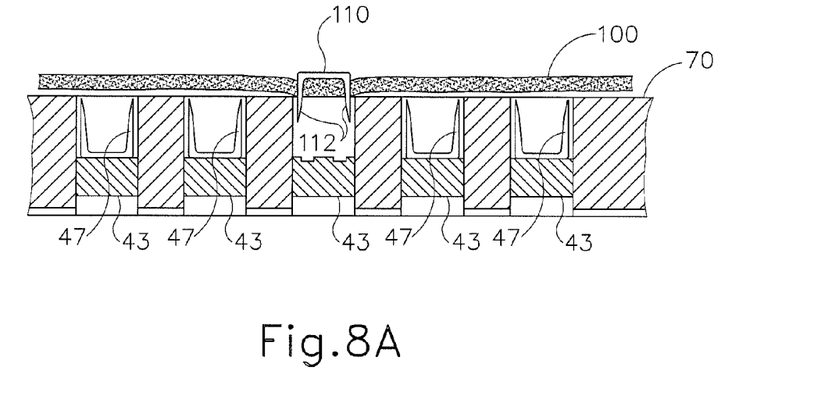
FIG. 8A depicts a side elevation view of the staple cartridge and buttress material of FIG. 7 in an unfired position.
Figure 8B:
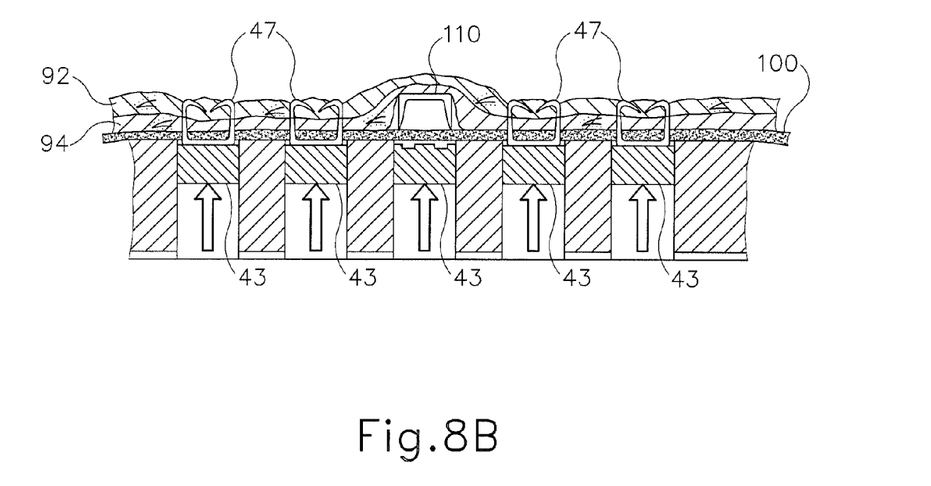
FIG. 8B depicts a side elevation view of the staple cartridge and buttress material of FIG. 8A in a fired position.
Figure 9:
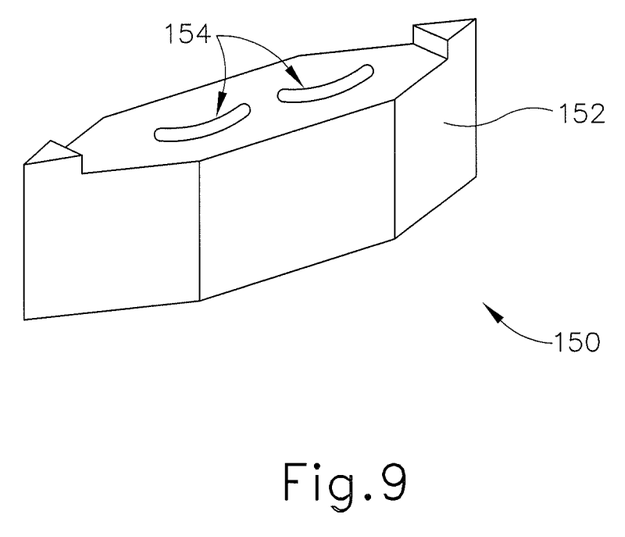
FIG. 9 depicts a perspective view of an exemplary attachment staple driver having staple forming pockets.

In some exemplary versions, staple cartridge (37) may be used in conjunction with a buttress material (100) as shown, for example, in FIGS. 7-9. It may be desirable to utilize buttress material (100) during the severing and/or stapling of tissue to aid in supporting and healing of the severed area. In the present example, buttress material (100) comprises a coagulant operable to buttress a surgical site when the surgical site is severed and stapled. For example, buttress material (100) may comprise fibrin and thrombin, but any suitable coagulant may be used as would be apparent to one of ordinary skill in the art in view of the teachings herein. Furthermore, buttress material (100) may comprise a hemostatic agent, any suitable glue material, acellular tissue (e.g., allogeneic or xenogeneic), collagen, gelatin, oxidized regenerated cellulose (ORC), degradable woven and non-woven synthetic materials such as polylactate, polyglycol, polycuproic acid, or any other suitable material as would be apparent to one of ordinary skill in the art in view of the teachings herein. In some exemplary versions, buttress material (100) may comprise a fibrin pad. Additionally, buttress material (100) may comprise any combination of a variety of suitable materials.

FIG. 7 depicts buttress material (100) placed on upper deck (70) and extending substantially along the length of upper deck (70). Buttress material (100) is a generally uniformly thick pad coupled to staple cartridge (37), but it will be appreciated that buttress material (100) may be distributed in discrete portions on upper deck (70). For example, strips of buttress material (100) may be used instead of a single pad. Such strips may include longitudinal strips, lateral strips, diagonal strips, etc. Alternatively, greater or lesser amounts of buttress material (100) may be positioned at the distal and/or proximal end of upper deck (70), though this is merely optional. It should be understood that any suitable distribution of buttress material (100) along upper deck (70) may be used as would be apparent to one of ordinary skill in the art in view of the teachings herein. Buttress material (100) of the present example comprises a semi-rigid and/or rigid structure such that, when decoupled from staple cartridge (37) as will be described below, buttress material (100) is able to generally maintain a flat, rectangular configuration.

Cartridge (37) of the present example has been modified such that one or more staple drivers (43), shown in FIGS. 8A-8B, do not have a staple (47) inserted therein. Instead, attachment staples (110) are inserted through buttress material (100) and into staple apertures (51) that correspond to those staple drivers (43) without a staple (47). In the example shown in FIG. 7, six attachment staples (110) are inserted through buttress material (100) and into staple apertures (51) to substantially secure buttress material (100) to upper deck (70) of staple cartridge (37). It should be understood that any number of attachment staples (110) may be used to couple buttress material (100) to staple cartridge (37). Attachment staples (110) each comprise a pair of resilient legs (112) that are biased outwardly from the main portion of each attachment staple (110). Accordingly, when attachment staples (110) are inserted through buttress material (100) and into staple apertures (51), resiliently biased legs (112) abut and selectively engage the sidewalls of staple apertures (51) to frictionally resist removal from within staple apertures (51). When staple cartridge (37) is used to deploy staples (47) via actuation of wedge sled (41), shown in FIGS. 3A-3B, the respective staple drivers (43) located below attachment staples (110) dislodge resiliently biased legs (112) from the sidewalls of staple apertures (51) such that attachment staples (110) are decoupled and driven out of their respective staples apertures (51), as will be discussed in more detail below in reference to FIGS. 8A-8B. As will be apparent to one of ordinary skill, the orientation of attachment staples (110) relative to upper deck (70) and the tissue is such that attachment staples (110) do not pierce the tissue when staples (47) are deployed from staple cartridge (37). For instance, attachment staples (110) may simply remain secured to buttress material (100), may fall freely into the surgical site, may be retained by a feature in anvil (18), etc.

Other suitable configurations for attachment staples (110) or other components to selectively couple and decouple from staple apertures (51) will be apparent to one of ordinary skill in the art in view of the teachings herein. For instance, in some versions attachment staples (110) may comprise a wire having a diameter that is larger than the diameter of the wire used for staples (47). Accordingly, the resiliently biased legs (112) may also be selectively secured to staple apertures (51) due the interference fit of the larger diameter wire within the staple aperture (51). In a further version, attachment staples (110) may include barbs (114) configured to dig into the material of staple apertures (51) to resist removal. Alternatively, rectangular insertable members (not shown) may be used instead of attachment staples (110). Such insertable members may include barbs (114) to resist removal as well. Further still, an adhesive may be included between upper deck (70) and buttress material (100) to further, or alternatively, secure buttress material (100) to upper deck (70).

FIG. 8A depicts staple cartridge (37) having buttress material (100) coupled to upper deck (70) by attachment staple (110). A plurality of staples (47) are also shown in an undeployed state atop staple drivers (43). FIG. 8B depicts buttress material (100) deployed with staples (47) and coupled to tissue (90). As shown in FIG. 8A, staples (47) are initially loaded into staple apertures (51) of staple cartridge (37) and positioned atop staple drivers (43) in an undeployed state. In the example shown, one staple aperture (51) does not receive a staple (47) therein. Instead, once buttress material (100) is laid atop upper deck (70), attachment staple (110) is inserted and selectively secured within staple aperture (51). While a single attachment staple (110) is shown, it should be understood that more than one attachment staple (110) may be used. By way of example only, three attachment staples (110) may be used per side of staple cartridge (37) to secure buttress material (100) thereto. As shown in FIG. 8A, staple cartridge (37) having buttress material (100) coupled thereto is in the undeployed state and is ready to be used to staple tissue.

When tissue (90) has been positioned atop staple cartridge (37) to be stapled and severed, the user then actuates closure trigger (26) to secure tissue (90) between anvil (18) and buttress material (100). The user then actuates firing trigger (28) to actuate firing bar (14) distally through staple cartridge (37). As described above, cutting edge (48) of firing bar (14) enters vertical slot (49) of staple cartridge (37), severing tissue clamped between staple cartridge (37) and anvil (18). Middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51), through buttress material (100), through tissue (90), and into forming contact with staple forming pockets (53) on the inner surface of anvil (18). Wedge sled (41) also drives the respective staples drivers (43) into attachment staples (110), thereby dislodging resiliently biased legs (112) and ejecting attachment staples (110) from staple apertures (51), as shown in FIG. 8B. Accordingly, staples (47) both staple tissue (90) and secure buttress material (100) to tissue (90) when deployed from staple cartridge (37). It should be understood that in the present example, attachment staples (110) are merely dislodged from staple cartridge (37) and do not couple to tissue (90). In some versions, resiliently biased legs (112) may comprise blunt tips.

Of course other configurations for attachment staples (110) and/or staple cartridge (37) will be apparent to one of ordinary skill in the art in view of the teachings herein. For instance, as shown in FIG. 9, an exemplary attachment staple driver (150) may be included in staple cartridge (37) at the respective staple apertures (51) where attachment staples (110) are to be inserted. Attachment staple driver (150) of the present example comprises a driver body (152) and staple forming pockets (154) formed on the surface of driver body (152). Staple forming pockets (154) of the present example are configured to engage and bend resiliently biased legs (112) into curled staple legs. Accordingly, when buttress material (100), staples (47), and attachment staples (110) are coupled to tissue (90) within a body, the curled resiliently biased legs (112) may form a smooth surface such that other tissue may not catch upon resiliently biased legs (112). Of course other versions and configurations for staple cartridge (37) and/or buttress material (100) will be apparent to one of ordinary skill in the art in view of the teachings herein. By way of example only, staple cartridge (37) and/or buttress material (100) may be constructed in accordance with at least some of the teachings of U.S. patent application Ser. No. 13/233,664, entitled "Surgical Instrument and Buttress Material," filed Sep. 15, 2011, the disclosure of which is incorporated by reference herein.

While certain configurations of exemplary surgical instruments have been described, various other ways in which the surgical instruments may be configured will be apparent to those of ordinary skill in the art in view of the teachings herein. By way of example only, the surgical instruments referred to herein may be constructed in accordance with at least some of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and U.S. Pat. No. 7,721,930.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a surgical instrument, wherein the surgical instrument is operable to sever and staple a portion of tissue, wherein the surgical instrument comprises a distal end, and wherein the surgical instrument comprises an end effector at the distal end; and
   (b) a staple cartridge, wherein the staple cartridge is selectively insertable into the end effector, the staple cartridge comprising:
      i. an upper deck,
      ii. a buttress material in communication with the upper deck, and
      iii. an attachment staple driver,
      wherein the buttress material is selectively coupled to the staple cartridge by one or more fasteners,
      wherein the attachment staple driver is operable to engage the one or more fasteners, and wherein the attachment staple driver is operable to decouple the one or more fasteners.

2. The apparatus of claim 1 wherein the one or more fasteners comprises an attachment staple, wherein the attachment staple selectively couples the buttress material to the upper deck.

3. The apparatus of claim 2 wherein the upper deck comprises an attachment staple aperture, wherein the attachment staple is inserted into the attachment staple aperture.

4. The apparatus of claim 3 wherein the attachment staple comprises a wire, wherein the wire has a diameter, wherein the attachment staple aperture has a width, and wherein the diameter of the wire is greater than the width of the attachment staple aperture.

5. The apparatus of claim 3 wherein the attachment staple comprises a wire, wherein the wire has a diameter, wherein the attachment staple aperture has a width, and wherein the diameter of the wire is substantially equal to the width of the attachment staple aperture.

6. The apparatus of claim 3 wherein the staple cartridge further comprises a plurality of staples and a plurality of staple drivers disposed therein, wherein the upper deck comprises a plurality of staple apertures, wherein each staple of the plurality of staples is in communication with a respective staple driver of the plurality of staple drivers.

7. The apparatus of claim 6 wherein the attachment staple aperture is longitudinally aligned with one or more of the staple apertures.

8. The apparatus of claim 6 wherein the plurality of staple drivers are operable to drive the plurality of staples through the buttress material.

9. The apparatus of claim 3 wherein the attachment staple driver is in communication with the attachment staple aperture.

10. The apparatus of claim 9 wherein the attachment staple driver is vertically translatable relative to the upper deck.

11. The apparatus of claim 9 wherein the attachment staple driver comprises staple forming pockets.

12. The apparatus of claim 2 wherein the attachment staple comprises a pair of resiliently biased legs.

13. The apparatus of claim 12, wherein the resiliently biased legs are biased outwardly.

14. The apparatus of claim 12 wherein the resiliently biased legs comprise barbs.

15. The apparatus of claim 1 wherein the buttress material is selected from a group consisting of:
    a hemostatic agent;
    thrombin; or
    fibrin.

16. An apparatus comprising:
    (a) a surgical instrument comprising an anvil, a lower jaw, and a firing bar having a cutting edge, wherein the anvil and the lower jaw are operable to secure a portion of tissue therebetween, wherein the firing bar is operable to advance distally relative to the anvil and lower jaw to cut the portion of tissue; and
    (b) a staple cartridge, wherein the staple cartridge is selectively insertable into the lower jaw, the staple cartridge comprising:
       i. a cartridge body,
       ii. an upper deck having a plurality of staple apertures formed therethrough,
       iii. a plurality of staple drivers, wherein each staple driver of the plurality of staple drivers is in communication with a respective staple aperture of the plurality of staple apertures,
       iv. one or more staples disposed in the cartridge body, wherein the one or more staples are in communication with one or more staple drivers of the plurality of staple drivers, and
       v. a buttress material in communication with the upper deck,
    wherein the buttress material is selectively coupled to the staple cartridge by at least one fastener; and
    wherein at least one staple driver of the plurality of staple drivers is operable to selectively decouple the buttress material from the staple cartridge.

17. The apparatus of claim 16 wherein the at least one fastener comprises a plurality of attachment staples, wherein each attachment staple of the plurality of attachment staples is inserted into a staple aperture.

18. The apparatus of claim 17 wherein each attachment staple of the plurality of attachment staples comprises a pair of resiliently biased legs.

19. The apparatus of claim 18 wherein the at least one staple driver of the plurality of staple drivers selectively engages the resiliently biased legs of at least one attachment staple of the plurality of attachment staples.

20. A method for selectively coupling a buttress material to a staple cartridge for a surgical instrument using one or more attachment members, wherein the surgical instrument comprises an end effector configured to receive the staple cartridge, wherein the end effector is operable to cut a portion of tissue and to staple a portion of tissue when the staple cartridge is inserted therein, wherein the staple cartridge comprises an upper deck having a plurality of staple apertures and a staple driver, the method comprising:
  (a) placing the buttress material on top of at least a portion of the upper deck; and
  (b) inserting the one or more attachment members through the buttress material and into at least one staple aperture of the plurality of staple apertures;
  wherein the insertion of the one or more attachment members selectively couples the buttress material to the staple cartridge, and wherein the staple driver is operable to selectively decouple the one or more attachment members.

* * * * *